United States Patent [19]

Anderson

[11] Patent Number: 4,531,523
[45] Date of Patent: Jul. 30, 1985

[54] DIGITAL GAIN CONTROL FOR THE RECEPTION OF TELEMETRY SIGNALS FROM IMPLANTED MEDICAL DEVICES

[75] Inventor: Katherine H. Anderson, Minneapolis, Minn.

[73] Assignee: Medtronic, Inc., Minneapolis, Minn.

[21] Appl. No.: 657,446

[22] Filed: Oct. 4, 1984

[51] Int. Cl.³ ............................................. A61N 1/00
[52] U.S. Cl. ............................ 128/419 PT; 128/696
[58] Field of Search .................. 128/419 PG, 419 PT, 128/696,903

[56] References Cited

U.S. PATENT DOCUMENTS

| | | | |
|---|---|---|---|
| 4,232,679 | 11/1980 | Schulman | 128/419 PG |
| 4,257,423 | 3/1981 | McDonald et al. | 128/419 PG |
| 4,325,384 | 4/1982 | Blaser et al. | 128/419 PG |

FOREIGN PATENT DOCUMENTS 2826189 1/1979 Fed. Rep. of Germany ...... 128/419 PG

Primary Examiner—William E. Kamm
Attorney, Agent, or Firm—Joseph F. Briemayer; Glenn W. Bowen; John L. Rooney

[57] ABSTRACT

A gain control system for verifying the programming of an implanted medical device is provided for an external programming unit which receives transmitted signals from the implanted unit and verifies if these signals represent valid "1" and "0" data bits. If the signals of an encoded message unit are valid signals then processing continues. If some of the signals are invalid due to noise interference, the gain of the receiver of the programming unit is decremented in steps as long as the error rate exceeds a predetermined number of errors per unit time.

2 Claims, 3 Drawing Figures

DIGITAL GAIN CONTROL FOR THE RECEPTION OF TELEMETRY SIGNALS FROM IMPLANTED MEDICAL DEVICES

BACKGROUND OF THE INVENTION

Implanted medical devices such as heart pacemakers are often programmed to use telemetric signals that are generated by a remote programming unit. Verification of the programming of implanted device is provided by the transmission of signals from the device to a receiving section of the programming unit. The programming signals are digital signals which are coded in some manner to signify logic 1 and 0 signals. In the disclosed embodiment, the encoding employs pulse interval modulation, wherein the intervals between bursts of high frequency pulses are long or short depending on the logic level of the data bit being transmitted.

Signals from implanted devices in a hospital environment are often subject to a relatively high level of noise, or interference. As long as the signal level is greater than the noise level, however, the gain of the receiver may be adjusted so that the noise level will be less than a threshold level. The information content of the coded signal is then employed to adjust the gain of the receiver. When errors occur in the message being sent from the implanted device, the number of errors in the repeated signal are counted over a period of time. If more than a predetermined number of errors occur in that time, the gain will be adjusted by a predetermined amount, and the signal will be continually monitored to determine if the adjusted gain level has eliminated the errors. The adjustment continues until all of the bits of the encoded information are received without error, and then further processing of received data from the implanted device is allowed to proceed.

DESCRIPTION OF THE DRAWINGS

The present invention is described by reference to the drawings in which.

TECHNICAL DESCRIPTION OF THE INVENTION

The digital gain control implementation of the present invention may be utilized in a remote programming device for programming an implanted medical device such as a heart pacemaker in order to confirm that the program transmitted to the device has been implemented. In a hospital environment, the electrical noise level is often very high, and signals transmitted from the implanted device must be received and detected despite high level of background noise.

Figure 1:
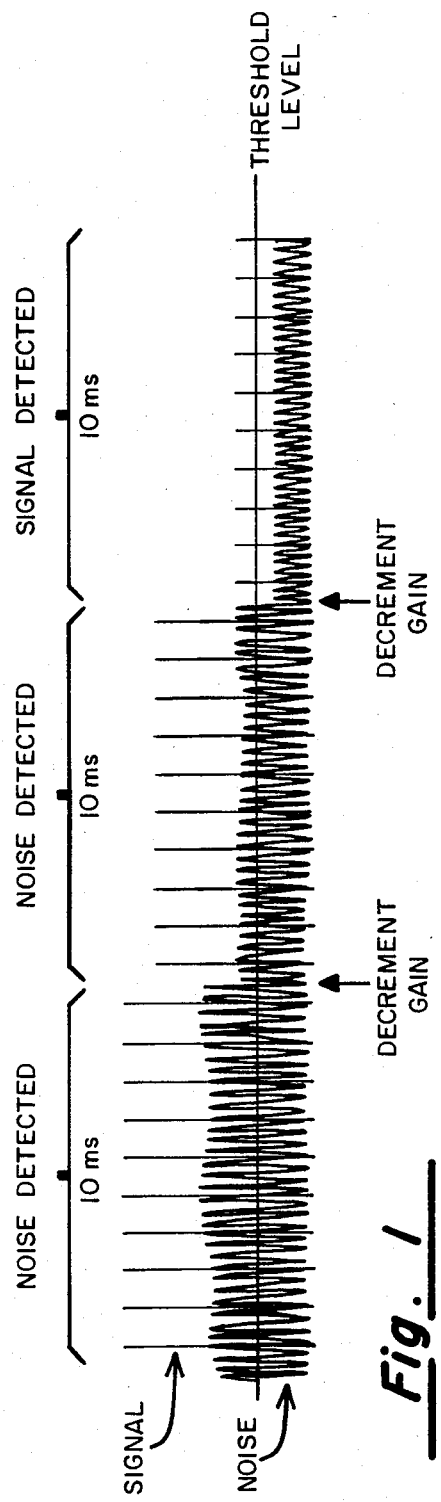
FIG. 1 is a diagramatic illustration of an incoming signal containing both telemetry information and noise at different gain settings relative to a threshold level.

FIG. 1 shows a series of information containing signals which are labeled "signal" which extend above the background noise level, which is labeled "noise". However, the noise level does initially extend above the threshold level of the receiver, and therefore, the noise will cause errors in the received signal. The implanted device continually transmits an encoded predetermined message to the remote programming device. The gain will be decremented in 10 ms steps as long as the noise remains above the threshold level. When the noise drops below the threshold level so that only the signal is above the threshold the gain is no longer decremented.

Figure 2:
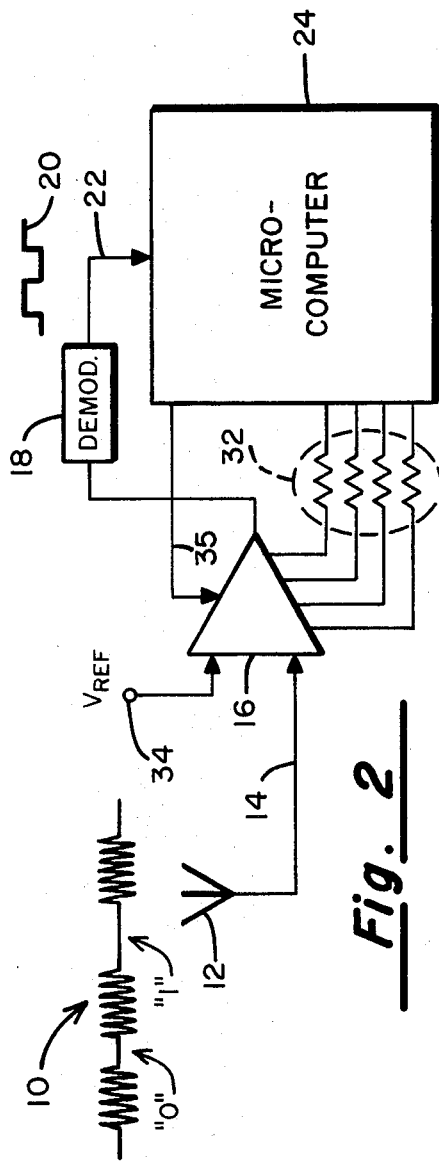
FIG. 2 is a block diagram of this system of the present invention.

FIG. 2 shows a portion of the receiving section of the programming device which illustrates that the incoming signal 10, which may contain both signal and noise, is received by the antenna 12 and coupled on the line 14 to an amplifier 6. A reference voltage is coupled on the terminal 34 to establish a threshold level. The output of the amplifier 16 is coupled to a demodulator which forms the pulses 20 consisting of the envelopes of the burst of the high frequency incoming signals. The pulses 20 provides the digital encoded information that is received from the implanted device which can be distinguished from the noise when the gain has been adjusted so that the noise falls below the threshold level.

The spacing of the pulses 20 defines whether a 1 or a 0 bit has been transmitted. Information can be readily detected once the noise is below the threshold level. This signal is coupled onto line 22 to a microcomputer 24, where the pulse interval modulated signal is decoded to determine if the implanted device has been transmitting the correct signals. If the transmitted signals are correct, the programming device will indicate to the implanted device that processing of additional information may take place, and the implanted device will send further digitally encoded signals to the amplifier 16 which will be coupled through the demodulator 18 and the input line 22 to be processed.

Gain control is achieved with the output lines 32 from the microcomputer 24 to the amplifier 16, which allows the amplifier to select various combinations of the input resistors in series with the lines which control the gain of the amplifier. Alternately, the threshold level of the amplifier could be varied by the microcomputer instead of the gain.

Figure 3:
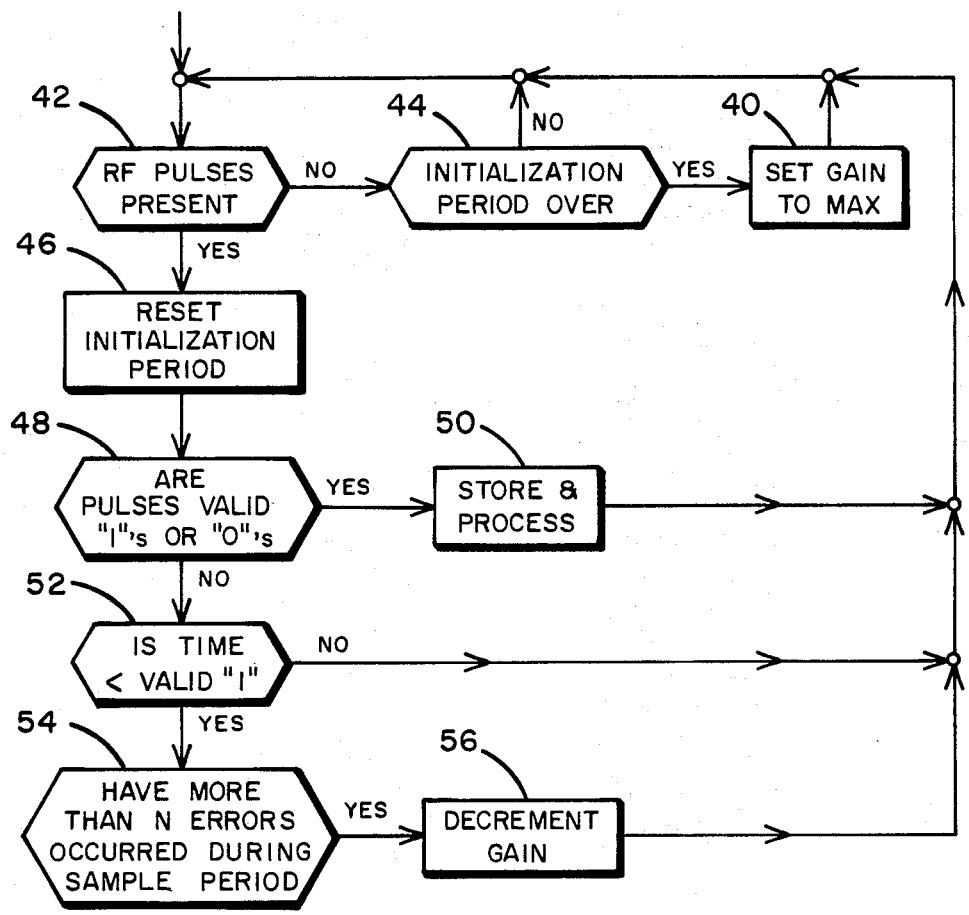
FIG. 3 is a flow chart diagram which illustrates the operation of the gain control portion of the programming device of the present invention.

The flow chart of FIG. 3 illustrates an implementation of the digital gain control system of the present invention. Initially the gain is set to a maximum and a sampling period is established, such as 10 ms, for example. The system is then activated to determine if any bursts of radio frequency (RF) pulses are present as indicated by step 42. If no RF pulses are present and the sampling, or initialization period of step 44 has expired, the gain will remain at a maximum, as indicated by step 40. However, if there are RF pulses present during the sampling period, the timing of the sampling period will be reset as indicated at step 46 so that the sampling period will be continually started following the termination of the previous sampling period as long as RF pulses are present.

Once the RF pulses have been received and have been transmitted by the demodulator 18 to the microcomputer 24, the microcomputer verifies whether all of the pulses are associated with valid 1 and 0 data bits, as indicated by step 48. The manner in which this is done is currently employed in pulse interval modulation systems by utilizing a high frequency clock which produces pulses that are much narrower than the width of the pulses of the waveform 20. For example, the pulses in the waveform 20 may be 1000 times wider than the width of the clock pulse. The number of pulses from this high frequency clock which occur while the waveform 20 is at a high level are counted and this count indicates the width and the spacing between pulses of the waveform to a very precise degree. Spacing between the pulses of the waveform 20 may also be readily determined by the microprocessor utilizing either software control or hardware implementation by other methods well known to those skilled in the art.

In the event that all of the pulses that are initially sampled in step 48 are valid "1's" and "0's", the programming unit will transmit a validation signal to the implanted device. The implanted device upon receipt of the validation signal will then transmit further signals to the programming device, and storage and processing of the transmitted data will continue as indicated by step 50. However, should there be errors in the encoded message transmitted from the programming device, further processing will not continue until all of the pulses of an encoded message are validated.

A second sampling period is employed during the reception of the encoded message at step 52, which is utilized to count the number of the pulses 20 which have occurred which do not prove to be either a valid 1 or a 0 signal. This is done by measuring the interval between pulses, and if the pulse interval is less than that required for a valid "1", the pulse is counted as an error pulse. If the number of invalid pulses exceed a predetermined number N over this period of time, the gain of the unit will be decremented one step as indicated by the steps 54 and 56. Further processing will then continue in the loop until the gain has been decremented to its minimum value, and either no verification is possible, or until the gain has been decremented to the point where the noise signal falls below the established threshold level and valid signals are being received.

In the event that there are some invalid level transitions detected at step 52, but the error rate is not sufficiently high to meet the condition of step 54, the gain will remain at the set level, but further processing will not continue. This condition will be generally a temporary one since the background noise will generally either diminish or increase to change the signal to noise level and the response of the system.

The present invention has been described with reference to a gain control system in which the gain is decremented. It will be apparent to those skilled in the art that increasing the gain would also come within the scope of the present invention. Furthermore, while the gain has been adjusted in the described embodiment, it will be apparent to those skilled in the art that the threshold level could alternately be varied in accordance with the scope of the present invention.

What is claimed is:

1. A gain control system for verifying the programming of an implanted medical device wherein the programmed implanted device transmits telemetry confirmation signals to a programming means with a variable-gain receiving means after the programming of said implanted device, wherein said signals are encoded binary signals that comprise a plurality of bits; comprising:

means for establishing the response of said receiving means so that said response may be altered to eliminate noise when the signal level exceeds the noise level;

means for verifying that the encoded signals sent from said implanted device represent valid 1 and 0 data bits;

means for processing further information from said implanted device only if all of the bits of said encoded signals are verified as valid 1 and 0 data bits;

means for establishing a sampling period and for determining the number of error bits in said signals which are caused by noise and which do not correspond to correct data bits of said encoded signals during said period of time; and means for varying said response by a predetermined amount when the number of said error bits exceed a predetermined amount during one of said periods of time so that said response relative to a threshold level is altered.

2. A gain control system as claimed in claim 1 wherein said response of said receiving means is a gain response and the gain of said receiving means is decremented so that said noise level is eventually reduced below said threshold level.

* * * * *